US008623656B2

(12) United States Patent
Komatsu et al.

(10) Patent No.: US 8,623,656 B2
(45) Date of Patent: Jan. 7, 2014

(54) SCREENING METHOD FOR TEST SPECIMEN

(75) Inventors: Manabu Komatsu, Atsugi (JP); Hiroyuki Hashimoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/052,272

(22) Filed: Mar. 21, 2011

(65) Prior Publication Data

US 2011/0171363 A1 Jul. 14, 2011

Related U.S. Application Data

(62) Division of application No. 12/542,201, filed on Aug. 17, 2009, now abandoned, which is a division of application No. 10/553,660, filed as application No. PCT/JP2004/019716 on Dec. 22, 2004, now abandoned.

(30) Foreign Application Priority Data

Dec. 22, 2003 (JP) ................................. 2003-424994
Sep. 24, 2004 (JP) ................................. 2004-277678

(51) Int. Cl.

| | |
|---|---|
| ***G01N 35/00*** | (2006.01) |
| ***G01N 1/00*** | (2006.01) |
| ***G01N 15/06*** | (2006.01) |
| ***G01N 33/48*** | (2006.01) |

(52) U.S. Cl.

USPC ............... 436/46; 436/43; 436/174; 436/180; 422/501; 422/509; 422/515; 422/68.1

(58) Field of Classification Search

USPC .................. 436/43–44, 46, 54–56, 174, 180; 422/501, 509, 511, 515–516, 518, 521, 422/536, 63–68.1

See application file for complete search history.

(56) References Cited

U.S. PATENT DOCUMENTS

| | | | |
|---|---|---|---|
| 5,365,563 | A | 11/1994 | Kira et al. |
| 6,024,925 | A | 2/2000 | Little et al. |
| 6,221,653 | B1 | 4/2001 | Caren et al. |
| 6,461,812 | B2 | 10/2002 | Barth et al. |
| 6,476,215 | B1 | 11/2002 | Okamoto et al. |

(Continued)

FOREIGN PATENT DOCUMENTS

| | | | |
|---|---|---|---|
| EP | 0655618 | A2 | 5/1995 |
| JP | 4-361055 | A | 12/1992 |

(Continued)

OTHER PUBLICATIONS

J.Y. Xu et al.,"Rapid Screening of Molecular Arrays Using Imaging TOF-SIMS", 203-204 Applied Surface Science 201-04 (2003).
Paolo Lazzeri et al., "Use of Spin-Coated TXRF Reference Samples for ToF-SIMS Metal Contaminant Quantification on Silicon Wafers," 29 Surf. Interface Anal. 798-803 (2000).

*Primary Examiner* — Brian R Gordon
(74) *Attorney, Agent, or Firm* — Fitzpatrick, Cella, Harper & Scinto

(57) ABSTRACT

A test specimen that has one or more chemical substances fixed to prescribed plural independent positions on a substrate, and the quantities of the chemical substances fixed at the respective prescribed positions are the total of integer multiples of existence quantity units defined for the respective chemical substances in the range from 1 amol to 1 nmol (excluding the case in which the total quantity is zero).

6 Claims, 3 Drawing Sheets

(56) References Cited

U.S. PATENT DOCUMENTS

| | | | |
|---|---|---|---|
| 6,485,913 | B1 | 11/2002 | Becker et al. |
| 6,579,139 | B1 | 6/2003 | Mishima et al. |
| 6,656,432 | B1 | 12/2003 | Hirota et al. |
| 6,787,313 | B2 | 9/2004 | Morozov et al. |
| 6,849,111 | B2 | 2/2005 | Suzuki et al. |
| 7,097,809 | B2 | 8/2006 | Van Dam et al. |
| 7,285,422 | B1 | 10/2007 | Little et al. |
| 7,332,271 | B2 | 2/2008 | O'Keefe et al. |
| 7,351,376 | B1 | 4/2008 | Quake et al. |
| 7,390,463 | B2 | 6/2008 | He et al. |
| 2002/0015958 | A1 | 2/2002 | Audeh et al. |
| 2002/0061598 | A1 | 5/2002 | Mutz et al. |
| 2002/0064482 | A1 | 5/2002 | Tisone et al. |
| 2003/0049862 | A1 | 3/2003 | He et al. |
| 2004/0005620 | A1 | 1/2004 | Okada et al. |
| 2004/0070655 | A1 | 4/2004 | Aoi et al. |
| 2004/0096976 | A1 | 5/2004 | Carlson |
| 2004/0110303 | A1 | 6/2004 | Carlson |
| 2004/0132080 | A1* | 7/2004 | Kawaguchi et al. .............. 435/6 |
| 2005/0106754 | A1 | 5/2005 | Caren et al. |
| 2005/0112029 | A1 | 5/2005 | Webb |
| 2005/0168551 | A1 | 8/2005 | Deardurff et al. |
| 2006/0065528 | A1 | 3/2006 | Lopez et al. |
| 2006/0154248 | A1 | 7/2006 | McGrew et al. |
| 2007/0212266 | A1 | 9/2007 | Johnston et al. |
| 2008/0069735 | A1 | 3/2008 | Chari et al. |
| 2009/0093373 | A1* | 4/2009 | Kawaguchi et al. .............. 506/9 |

FOREIGN PATENT DOCUMENTS

| | | | |
|---|---|---|---|
| JP | 7-151714 | A | 6/1995 |
| JP | 11-187900 | A | 7/1999 |
| JP | 2000-251665 | A | 9/2000 |
| JP | 2003-254971 | A | 9/2003 |
| JP | 2004-226280 | A | 8/2004 |
| WO | 01/29561 | A1 | 4/2001 |
| WO | 01/83825 | A1 | 11/2001 |

* cited by examiner

SCREENING METHOD FOR TEST SPECIMEN

CROSS-REFERENCE TO RELATED APPLICATIONS

This application is a division of application Ser. No. 12/542,201, filed Aug. 17, 2009, which is a division of application Ser. No. 10/553,660, which is the U.S. national stage of International Application No. PCT/JP2004/019716, filed Dec. 22, 2004, which claims priority from Japanese Patent Application Nos. 2003-424994, filed Dec. 22, 2003, and 2004-277678, filed Sep. 24, 2004. All prior applications are incorporated herein by reference.

TECHNICAL FIELD

The present invention relates to a test specimen having a chemical substance fixed at plural positions on a substrate and to a screening method employing the test specimen.

BACKGROUND ART

With the development of film formation techniques in recent years, various materials and devices are becoming constructed mainly of thin films of 1 μm or thinner. Lately, high-speed film-formation techniques have been developed, which enable formation of a thin film structure by holding plural functional films on a substrate as a fine part of high functionality, such as electronic devices and bio-chips. Further, thin film structures having a sensor function, which detect a micro quantity of a chemical reaction product by utilizing plural components in the thin film, have become important.

With such improvements of the function of thin film parts, methods are being developed for more precise and finer analysis and evaluation of the thin films. The examples of the methods are:

(1) Direct measurement of electroconductivity, hardness, optical properties, X-ray reactivity, and ionic reactivity for measurement of functions of a thin film;

(2) Indirect analysis of the components of a thin film by fractionation of a thin film component by gas chromatography, high-speed liquid chromatography, ICP-MS analysis, or a like method;

(3) Marker insertion to an objective substance in the thin film, such as addition of a fluorescent functional substance, or substitution by an isotopic element;

and combinations thereof.

In particular, precise and accurate analysis of the film components is indispensable, because the functions of the thin film are affected delicately by the component ratios. The extremely small thickness of the thin film tends to cause a problem of dependence of the functions of the thin film on the state of the substrate for the thin film and a problem of an adverse effect of contamination with foreign matter or a change of the quality or quantity of the thin film by pretreatment. The dependence of the function of the thin film on the film component ratio is investigated frequently by formation of thin film samples constituted of various component concentration ratios, direct measurement of the function as mentioned in the above method (1), and preparation of a calibration curve regarding the dependency of the obtained signal intensity on the component concentration ratio. For preparation of a more accurate calibration curve, the components should be uniformly distributed in the thin film sample and there must be precise control of the component concentration ratio in the samples.

P. Lazzeri et al. (Surface and Interface Analysis, Vol. 29, 798 (2000)) describes formation of a thin film by spin coating and analysis thereof with a time-of-flight secondary ion mass spectrometer (hereinafter referred to as a “TOF-SIMS”). In this method, the size of one thin film is several millimeters square. This size is about ten thousand times the size of thin films used currently in devices in which the size of the one thin film is being decreased to tens of micrometers square. Such a large difference in the size causes a difference between the practical thin films and the thin films for calibration samples due to local flocculation and mixing state of the respective components, and other conditions. Therefore, ideally, the entire thin film is to be measured and analyzed at one time. However, one measurement region of the TOF-SIMS is as small as several hundreds of micrometers square, which cannot cover the entire thin film at once. Therefore, the measurement sectional regions are introduced successively into a measurement chamber for the measurement. In such a measurement process, during the waiting time for the measurement, the component ratio is liable to vary by adhesion of moisture or an impurity from the environmental atmosphere to the measurement regions or evaporation of the sample component from the measurement regions.

(1) Direct measurement of electrical conductivity, hardness, optical properties, X-ray reactivity, and ion reactivity as the thin film functionality.

Energy dispersive fluorescent X-ray analysis is capable of a simultaneous measurement of Na and heavier elements by use of a fluorescent X-ray. The fluorescent X-ray intensities are proportional in first approximation to the concentrations of the respective elements, but are affected greatly by ratio of coexisting component elements by absorption and secondary excitation effect thereof. Therefore, in the fluorescent X-ray analysis, the standard specimens for the calibration should also be prepared by strictly controlling the component mixing ratio for the quantitative determination of the film components and evaluating the functionality.

U.S. Pat. No. 5,365,563 evaluates the influence of the component mixing ratio in the thin film by a calculation in a quantitative determination by fluorescent X-ray measurement. In this method, however, precise calculation is difficult, because the fluorescent X-ray intensity is not necessarily in a linear relationship with the component ratio. Further, in this method, the samples should be prepared in a number corresponding to the number of the film components, which requires finally tested specimens of high accuracy for the quantitative determination.

Due to the above reasons, precise quantitative determination is not practicable in any of the conventional methods. Therefore, in many analysis methods including ionic analysis and fluorescent X-ray analysis, standard specimens should be prepared with accurate and precise control of the component concentration ratio.

DISCLOSURE OF THE INVENTION

According to an aspect of the present invention, there is provided a test specimen having one or more chemical substances fixed to prescribed plural independent positions on a substrate, wherein the quantities of the chemical substances existing in the respective prescribed positions are totals of integer multiples of existence quantity units defined for the respective chemical substances.

At least one kind of the fixed chemical substances is preferably applied onto the substrate by an inkjet system. All kinds of the fixed chemical substances are more preferably applied onto the substrate by an inkjet system.

The quantity of the chemical substance applied onto the prescribed positions by the inkjet system is preferably controlled by a number of liquid droplets which contain the chemical substance and ejected by the inkjet system. One liquid droplet has preferably a volume of not more than 50 pL.

The prescribed positions are preferably arranged in a matrix, and are different in the existing ratios of the chemical substance.

The chemical substance is preferably selected from the group consisting of metals, metal compounds, semiconductor materials, organic compounds of a number-average molecular weight of not more than 10,000, biological substances, metal ions, metal complexes, halogen ions, and substances having solubility of 1 ppb or more in water or an organic solvent at an ordinary temperature and pressure. The metal, the metal compound, or the semiconductor material is preferably applied in a state of a fine particle of a diameter of not larger than 1 μm.

The test specimen is preferably used as a standard sample for quantitative analysis. The quantitative analysis is more preferably conducted by time-of-flight secondary ion mass spectrometry (TOF-SIMS).

According to another aspect of the present invention, there is provided a screening method, wherein a test object is applied by inkjet system onto the chemical substance fixed to the prescribed positions on the above test specimen, and a reaction is detected.

The test object preferably contains a biological substance or a medical substance.

The reaction is preferably detected by time-of-flight secondary ion mass spectrometry (TOF-SIMS).

EFFECTS OF THE INVENTION

In the present invention, a test specimen is prepared quickly which contains components in varying ratio in a thin film in fine regions placed on a substrate for observing influences of slight change of constituting component ratio and contamination of impurity. With this test specimen, precise quantitative determination can be conducted. As shown later in Example 1, an effective calibration curve can be formed for the measurement in which a slight change of component like impurity contamination may cause change in the signal intensity. Further as shown later in Example 2, an effective calibration curve can be formed for the quantity of a chemical reaction product of plural mixture components.

BEST MODE FOR CARRYING OUT THE INVENTION

Figure 1:
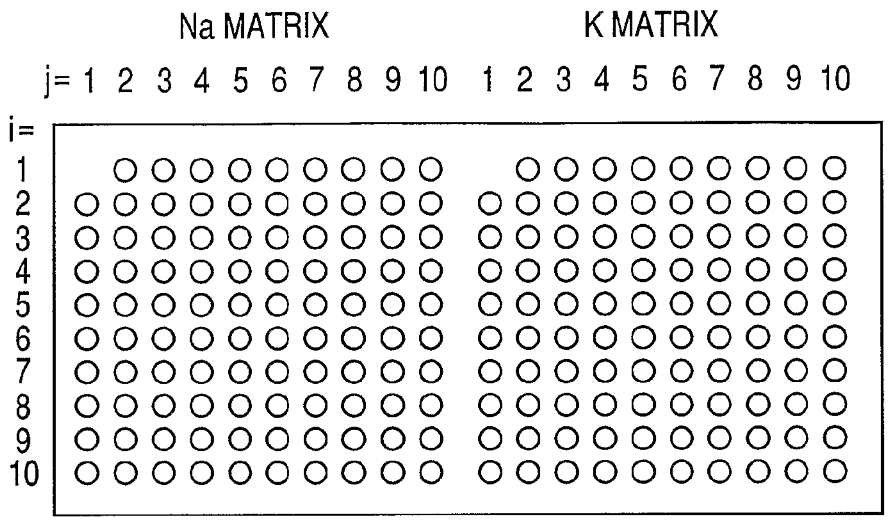
FIG. 1 illustrates schematically a planar arrangement of constitution elements in a quantitative determination specimen of the present invention.

In the test specimen of the present invention, one or more chemical substances are immobilized or fixed on each of prescribed positions on a substrate. The quantity of the chemical substance is separated by a quantity unit. The quantity unit by which represents the quantity of the chemical substance existing in the respective position is called an "existence quantity unit." Thereby, the quantity of each of the chemical substances at a prescribed position is indicated by an integer multiple of the existence quantity unit. For example, in the case where the existence quantity units of five chemical substances $\alpha$, $\beta$, $\gamma$, $\delta$, and $\epsilon$ are denoted respectively by a, b, c, d, and e, and four chemical substances $\alpha$, $\beta$, $\gamma$, $\delta$, and $\epsilon$ exist at a certain prescribed position, the sum of the quantities of the existing chemical substances is $c_1a+c_2b+c_3c+c_4d+c_5e=c_1a+c_2b+c_3c+0\times d+c_5e$, where $c_1$, $c_2$, $c_3$, $c_4$, and $c_5$ are respectively an integer, and the coefficient $c_4$ for d is zero because of the absence of the substance $\delta$.

When the chemical substance is fixed without volatilization or diffusion at the prescribed positions, the existence quantity unit is occasionally called a "fixation quantity unit."

The application and fixation of the chemical substance to a substrate is conducted suitably by an inkjet system typified by a bubble jet system. A region containing at least one kind of chemical substance can be formed by applying and fixing the chemical substance onto a substrate by an inkjet system (hereinafter the region is occasionally called a "fixation region"). Incidentally, a solution of chemical substance $\gamma$, for instance, is referred to a "$\gamma$ solution."

For precise control of the fixation quantity of chemical substances, the respective chemical substances are preferably applied separately and independently onto a substrate by an inkjet system. The inkjet system enables application of a necessary number of fine liquid droplets containing the chemical substance onto an intended spot. The application of plural liquid droplets of a chemical substance solution to mix the plural liquid droplets is called "superposed dotting" or "dotting in superposition" in this Specification. The volume of one liquid droplet applied by the inkjet system is preferably not more than 50 pL. Here the existence quantity unit is preferably defined by the quantity of the chemical substance contained in the one liquid droplet of the inkjet or an integer multiple thereof. Otherwise, the existence quantity unit may be defined to bring the integer multiple of the existence quantity unit within a suitable range in the calibration.

The test specimen of the present invention is constituted by controlled application of the chemical substance by an inkjet system. Therefore a precise calibration curve for quantitative analysis can be obtained by use of this test specimen.

For quantitative analysis by use of the test specimen of the present invention as a standard sample, the plural positions of the chemical substance fixation are preferably arranged in a matrix. The matrix arrangement is suitable for changing the fixation quantity of the chemical substance for the quantitative analysis. The fixation positions of the chemical substance are arranged in a matrix of X lines and Y columns. The matrix may be divided into submatrix elements. One submatrix is called a "block." The prescribed position constituting the matrix of the present invention is called an "element position." Of course, one block may consists of one element position. The composition having been applied to the element position and containing the chemical substance is called a "spot." The operation of registering the ejection head to the element position and applying the liquid droplets onto the element position by ejection is called "spotting." The spot formed by one liquid droplet is called a "dot." One liquid droplet traveling in the air for formation of a spot is also called a "dot" occasionally. The dot of a γ solution is called a "γ dot." Two or more dots may be put in superposition to form one spot. The operation of ejection or non-ejection of a droplet of a solution from an ejection head onto an element position is called an "application operation." The application operation includes stop of the head at an element position not to conduct spotting to the element position on the basis of the determination of applying no dot to the element position. One scanning cycle is completed by application operation of all the solution ejection heads respectively on every element position of the XY matrix.

The chemical substance in the present invention includes metals, metal compounds, semiconductor materials, organic compounds of a number-average molecular weight of not more than 10,000, biological substances, metal ions, metal complexes, halogen ions, and substances having solubility of 1 ppb or more in water or an organic solvent at an ordinary temperature and pressure. A metal, metal compound, or semiconductor material, on application onto a substrate, is preferably in state of a fine particles of not larger than 1 μm in diameter on the substrate.

The test specimen of the present invention is useful suitably as a standard specimen in quantitative analysis by time-of-flight secondary ion mass spectrometry (TOF-SIMS). A primary use of the test specimen is a standard specimen for quantitative analysis by time-of-flight secondary ion mass spectrometry (TOF-SIMS) and like analysis methods. The analysis methods by use of the test specimen of the present invention as a standard specimen include fluorescent X-ray analysis, optical response analysis, and electrical conductivity analysis in addition to the TOF-SIMS.

In quantitative analysis by TOF-SIMS, the dose quantity of primary ions is kept constant at a level of not higher than $1\times10^{13}/cm^2$, and the integrated intensity (count number) of specified secondary ions emitted from a prescribed area is measured.

A secondary use of the test specimen of the present invention is use for various screening. In the screening, a third chemical substance is applied by an inkjet system onto the chemical substance fixed on plural points on the test specimen and the resulting chemical reaction is used for the screening. The third chemical substance is preferably a biological substance or a medical substance. The test is preferably conducted by time-of-flight secondary ion mass spectrometry (TOF-SIMS).

When the objective chemical substance is a water-soluble metal complex, a material disclosed in Japanese Patent Application Laid-Open No. 2000-251665, for instance, can be used as it is. Such a material is preferably applied by a bubble jet system. The test specimen of the present invention prepared by applying a chemical substance solution onto a substrate by an inkjet system may be heat-treated, if necessary, after the application. The dotting in superposition by the inkjet system may be conducted with a driving system described in Japanese Patent Application Laid-Open No. H04-361055.

Before application of the test chemical substance onto the substrate, the substrate surface may be treated for fixation of the chemical substance. This treatment may be conducted, for instance, by the method described in Japanese Patent Application Laid-Open No. H11-187900. This method is preferably employed when the chemical substance to be applied is an organic compound having an SH group.

According to the present invention, a test specimen can be prepared for precise evaluation of the dependency of the performance of a thin film on a slight difference in the components ratio in the film, the film thickness, and the kind of the substrate. This is one of the features of the present invention.

For instance, the intensity of signals according to ionization is affected greatly by the state of a specimen. Therefore, dependence of a noticed function on the state of the specimen can be evaluated by using signals obtained from the ionization. For this evaluation, the test specimen of the present invention and preparation method thereof will be effective.

A generalized embodiment of the present invention is explained below. For simplicity of explanation, two kinds of chemical substances, α and β, are used to prepare a test specimen.

Solutions of the respective chemical substances are prepared, and are stored respectively in printer head tanks.

In this embodiment, the element positions are arranged in a matrix having X lines and Y columns. This XY matrix is divided into submatrixes having respectively m lines and n columns, where $m<n$. One submatrix is called a "block." The block on the i-th line on the j-th column of the XY matrix is represented by $B_{ij}$. For simplicity of explanation, all the blocks are assumed to be constituted of elements in x lines and y columns. Therefore, $x\cdot m=X$ and $y\cdot n=Y$.

All the spots fixed at element positions in one block are made to have the same composition within that block.

One droplet of an α solution ejected from a printer head is assumed to contain a chemical substance a in an amount of "a," and one droplet of a β solution ejected from a printer head is assumed to contain a chemical substance β in an amount of "b."

In one scanning cycle of the spotting operation, the spots may be formed on all the element positions in one block, and thereafter sequentially in the next blocks (this process being called a "sequence process." Otherwise, the spots may be formed on a specific element position in all of the blocks and then this application operation is repeated by changing the specific positions at all of the positions on all of the blocks (this process being called a "correspondence process").

Naturally, the heads may be provided in a number corresponding to the number of the lines or columns of the blocks to conduct the spotting operation on the respective lines or columns simultaneously.

In the first scanning cycle, a dots are put at all the element positions in all of the blocks except the blocks on the first line, and β dots are put at all the element positions in all of the blocks except the blocks on the first column.

In the second scanning cycle, a dots are put in superposition at all the element positions in all of the blocks except the blocks on the first and second lines, and β dots are put in superposition at all the element positions in all of the blocks except the blocks of the first and second columns.

Similarly, in the i-th scanning cycle, α dots are put in superposition at all the element positions in all of the blocks except the blocks of the first to i-th lines, and β dots are put in superposition at all the element positions in all of the blocks except the blocks of the first to i-th columns.

In the m-th scanning cycle, since there is no (m+1)th line, the dotting of the α solution is not conducted, and β dots are put in superposition at all the element positions in all of the blocks except the blocks of the first to m-th columns. Thus, in the m-th scanning cycle and later scanning cycles, the α solution is not applied.

In the (n−1)th scanning cycle, the α solution is not put, and β dots are put in superposition at all the element positions in the blocks except the 1 to (n−1)th columns, namely in the n-th column.

In the n-th scanning cycle, since there is no columns except the 1 to n columns, the β solution is not applied, and the scanning is completed.

After the above scanning cycles, no α dot is formed in the blocks on the first line, and no β dot is formed in the blocks on the first column: there is no spot in the block $B_{11}$.

In the block $B_{ij}$, the spot at one element position is formed by (i−1) a dots, and (j−1) β dots. Therefore, the quantity of the chemical substance α in that spot is a(i−1), and the quantity of the chemical substance β is b(j−1). Since each of the blocks has element positions in x lines and y columns, the block $B_{ij}$ contains totally the chemical substance a in a quantity of a(i−1)xy and the chemical substance β in a quantity of b(j−1)xy. For instance, in the block $B_{45}$, the number of the α dots is 4−1=3, and the number of the β dots is 5−1=4 for formation of the one spot on the respective element positions: the spot contains the chemical substance α in a quantity of 3a and the chemical substance β in a quantity of 4b. In the entire block $B_{45}$, the chemical substance α is contained in a quantity of 3axy, and the chemical substance β is contained in a quantity of 4bxy. In the above method, the concentration ratios are changed only by an integer ratio between the blocks. Dots having any existence ratio can be formed by providing plural aqueous solutions having different concentrations for standard specimen preparation.

A specimen having continuous condition change in the entire XY matrix can be prepared by varying the element positional conditions and subdividing the blocks, and conducting the spot formation by the aforementioned correspondence method to give conditional gradient in the one block.

EXAMPLES

The present invention is described below in more detail by reference to Examples. The examples below show best modes for carrying out the invention, but do not limit the invention thereto.

Example 1

In analysis of components of a biological material by SIMS or fluorescent X-ray analysis, a trace amount of sodium (Na) or potassium (K) as a contaminant may affect the intensity of the signals. In this Example, a calibration curve was obtained for quantitative determination of phosphorus (P) by TOF-SIMS by using a standard sample of ammonium phosphate ($NH_4H_2PO_4$, ammonium dihydrogenphosphate) containing Na and K as an example of quantitative determination of a biological material by using the method of the present invention.

(1) Substrate Cleaning

A silicon substrate (high-resistance p-type, commercial product) having a size of 10 mm×12 mm×1 mm was subjected to supersonic cleaning in high-purity acetone, ethanol, and ultrapure water respectively for 10 minutes.

(2) Preparation of Aqueous Solutions of Component Mixtures

Aqueous standard solutions for IPC-MS (SPEX Co.) containing respectively P (10.1%), Na (10.1%), or K (5.0%) were diluted respectively with pure water to 100 μM to prepare aqueous solutions for standard sample preparation (hereinafter referred to as a "P solution," an "Na solution, and a "K solution" respectively). Two standard specimens were prepared: a matrix having elements composed of mixtures of the P solution and the Na solution as the elements, and a matrix having elements composed of mixtures of the P solution and the K solution (hereinafter the former is referred to as an "Na matrix," and the latter is referred to as a "K matrix"). The spot formation procedure in this Example is shown below specifically for formation of the Na matrix from the P dots and the Na dots. For formation of the K matrix, the Na solution is replaced by the K solution in the Na matrix formation procedure.

(3) Application of Solutions for Preparation of Quantitative Determination Specimen by Inkjet System The printer employed was a bubble jet printer (BJF-950: Canon K.K.), which is a kind of a thermal jet printer. The above-prepared aqueous standard solutions were placed respectively in a several hundred microliter portion in the three tanks of the printer head of the printer. The volume of the one liquid droplet of the respective solutions ejected from the printer heads was 4 pL/droplet. The dot formed by one liquid droplet on the element position had a diameter of about 50 μm. The spots were formed by dotting in superposition. The content of P in one ejected droplet is $2.4\times10^8$ atoms and the content of Na therein is $2.4\times10^8$ atoms. The content of K in one ejected droplet regarding K matrix is also $2.4\times10^8$ atoms. The Na matrix and the K matrix were formed respectively of 157 lines and 236 columns at a density of 200 dpi, namely 127 μm pitch, in a range of 20 mm×30 mm on the surface of the silicon wafer having been cleaned in Step (1) above. The two matrixes were placed side by side as shown in FIG. 1. The Na matrix was divided into blocks in 10 lines and 10 columns. The reminders of the divisions were ignored.

In the first scanning cycle, P dots were applied on all lines except the first line, and Na dots were applied on all columns except the first column.

In the second scanning cycle, P dots were applied on all lines except the first and second lines in superposition on the spots having formed in the first scanning cycle, and Na dots were applied on all columns except the first and second columns in superposition on the having formed in the first scanning cycle.

In the later scanning cycles, the P dots and the Na dots were put in superposition by decreasing one line and one column of the application in each scanning cycle. That is, in the i-th scanning cycle, P dots were put in superposition on all the spots in all of the lines except the first to i-th lines, and Na dots were put in superposition on all the spots in all of the columns except the first to i-th columns.

In the ninth scanning cycle, the P dots were put only on the tenth lines, and the Na dots were put only on the tenth columns.

The pattern was completed by the above nine scanning cycles. In the block $B_{ij}$ on the i-th line on the j-th column, the spot at one element position is formed from (i−1) dots of P, and (j−1) dots of Na. Therefore, in that spot, the quantity of P is a(i−1), and the quantity of Na is b(j−1). When the number of the element position in the block $B_{ij}$ is $n_{ij}$, the total quantity of P in the block $B_{ij}$ is a(i−1)$n_{ij}$, and the total quantity of Na in this block is b(j−1)$n_{ij}$.

No dot was put on the first line on the first column in the block $B_{11}$ (at the upper left corner) of the Na matrix shown in FIG. 1, so that no spot was formed there.

Although a bubble jet printer was employed in this Example, the same result will be obtained by use of a piezo type printer or a like printer.

(4) TOF-SIMS Measurement

The concentration standard specimen shown in FIG. 1 was subjected to analysis by means of a time-of-flight secondary ion mass spectrometer (TOF-SIMSIV: ION-TOF Co.). The irradiation was conducted to a primary ion injection dose of $1\times10^{12}$ atoms/cm$^2$ under the conditions shown in Table 1, the intensity of P of the secondary ions detected during the irradiation was integrated, and the cumulative intensity was derived for the mixing ratios of Na or K.

TABLE 1

TOF-SIMS Measurement Conditions

| Primary ions | | Secondary ions | |
|---|---|---|---|
| Ion species | $Ga^+$ | Ion species | $C^-$ |
| Acceleration voltage | 25 kV | Measurement region | 300 × 300 μm$^2$ |
| Pulse | 10 kHz | Integration times | 32 times |

Figure 2A:
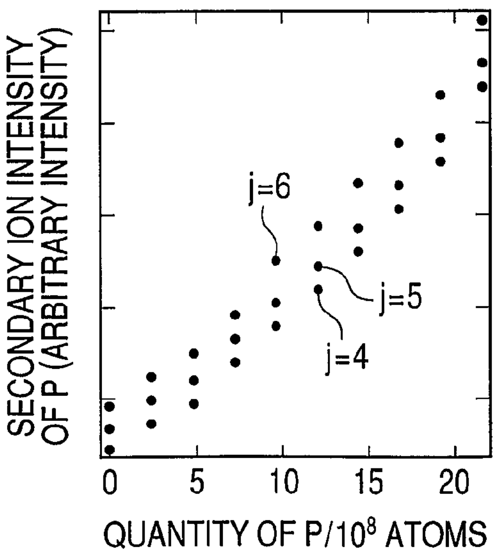
FIGS. 2A and 2B are graphs showing relations of a measured secondary ionic strength to a quantity of a substance in a dot in a quantitative determination specimen.
Figure 2B:
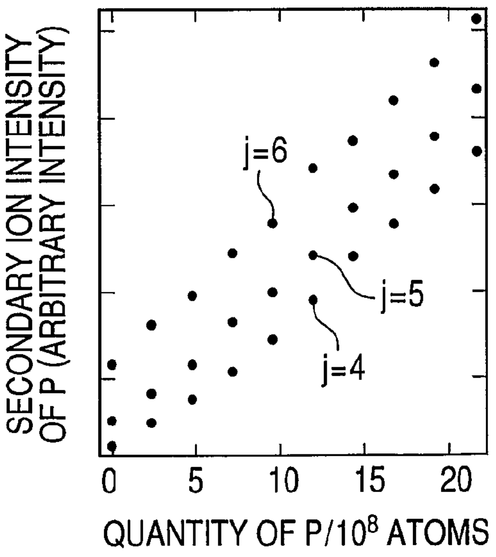

FIGS. 2A and 2B show relations between the intensity of phosphorus secondary ion and the quantity of existing phosphorus for each of the spots on the third line (j=4), the fourth line (j=5), and the fifth line (j=6) for each of the Na and K, respectively. The phosphorus secondary ion intensity increased slightly with increase of the mixed Na and K. Thus, the matrix effects of the impurities or the like can be quantitatively understood, which enables precise quantitative analysis by TOF-SIMS.

Example 2

By the technique of the present invention, an effective calibration curve can be obtained for the quantity of a product of a chemical reaction of mixture components. In this Example, a test specimen for a chemical reaction product was prepared by dropping an aqueous solution of sodium carbonate ($Na_2CO_3$) onto a film of a peptide (Morphiceptin: mass number 521 amu) formed on a substrate, and was evaluated.

An aqueous solution of Morphiceptin, a well-known intracerebral neurotransmitter, and an aqueous solution of sodium carbonate as a weak acid salt were prepared. Spots were formed by changing the quantity of the respective components by dotting in superposition by an inkjet system. The quantity of the chemical reaction product of the two components in the spot was evaluated by secondary ion intensity by TOF-SIMS.

(1) Preparation of Specimen

Figure 3:
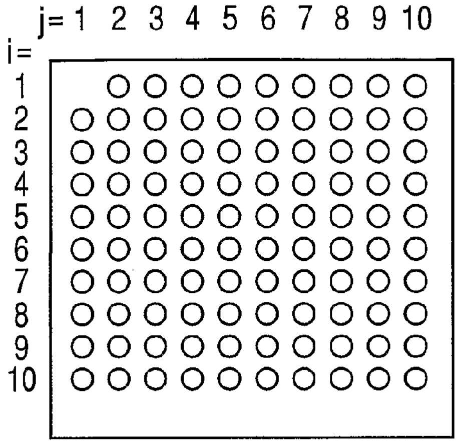
FIG. 3 illustrates schematically a planar arrangement of constitution elements in a quantitative determination specimen of the present invention.

Morphiceptin and powdery sodium carbonate were dissolved respectively in water to prepare an aqueous Morphiceptin solution ($1.9\times10^4$ mol/L) and an aqueous sodium carbonate solution ($2.4\times10^4$ mol/L). Spots were formed on a silicon wafer surface as shown in FIG. 3 by a bubble jet printer in the same manner as in Example 1. In the block $B_{ij}$ on the i-th line on the j-th column, the spot at one element position is formed by (i−1) dots of Morphiceptin, and (j−1) dots of sodium carbonate. Therefore, in that spot, the quantity of Morphiceptin is a(i−1) and the quantity of sodium carbonate is b(j−1), where “a” and “b” are respectively a quantity of Morphiceptin or sodium carbonate contained in one ejected liquid droplet. When the number of the element position in the block $B_{ij}$ is $n_{ij}$, the total quantity of Morphiceptin in the block $B_{ij}$ is $a(i-1)n_{ij}$, and the total quantity of Na is $b(j-1)n_{ij}$ in this block.

(2) TOF-SIMS Measurement

The concentration standard specimen shown in FIG. 3 was subjected to TOF-SIMS measurement. The intensity of ions formed from the molecular Morphiceptin (hydrogen atom addition, mass number 522 amu), and the intensity of ions (mass number: 544 amu) of the chemical reaction product (Morphiceptin molecule+sodium) ions were integrated, and the cumulative intensities for the chemical reaction product was derived for the existence ratios of the substances.

Incidentally, the chemical reaction of the Morphiceptin molecule and sodium carbonate is substitution of the hydrogen atom of the terminal carboxyl group (COOH) of the Morphiceptin molecule by sodium.

Figure 4A:
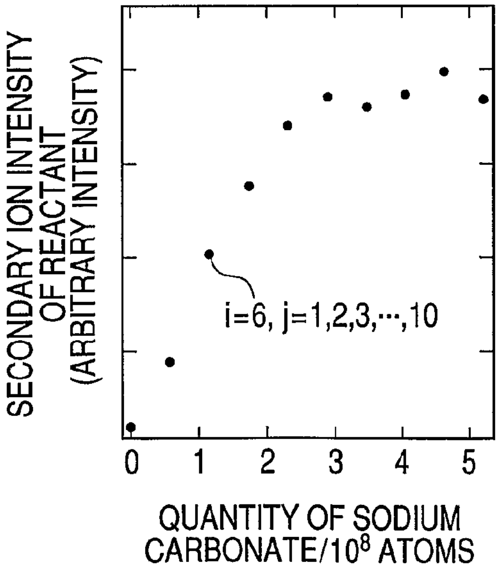
FIGS. 4A and 4B are graphs showing relations of measured secondary ionic strengths of a chemical reaction product and an unreacted substance to a quantity of a substance in a dot in a quantitative determination specimen.
Figure 4B:
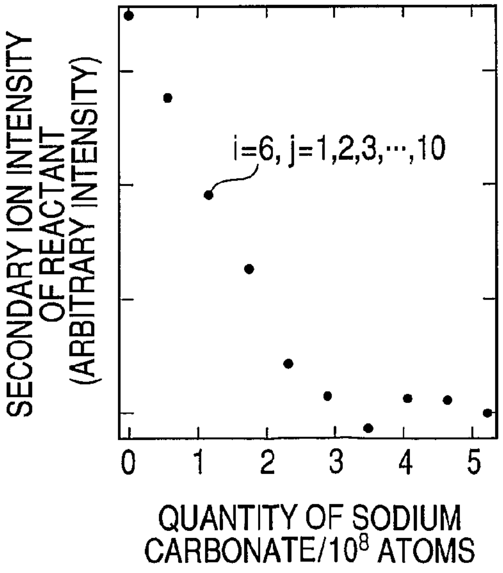

FIGS. 4A and 4B show the dependency of the average of the secondary ionic intensities of the reaction product (Morphiceptin molecule+sodium) and the unreacted reactant (Morphiceptin molecule+hydrogen) on the existence quantity of sodium carbonate in each of the spots at the positions of i=6 (fixed) and j=1, 2, 3, . . . , 10. As shown in FIGS. 4A and 4B, before the chemical equilibrium, the secondary ion intensity of the chemical reaction product in the presence of molecular sodium carbonate increases in linear proportion, and the secondary ion intensity of the unreacted reactant decreases in linear proportion.

Example 3

This Example shows detection of plural parent peptide molecular moieties by TOF-SIMS.

(1) A silicon wafer substrate was prepared in the similar manner as in Example 1.

(2) A first synthetic peptide SEQ ID NO: 1 (GGGGCGGGGG) (hereinafter referred to as a “peptide G,” mass number: 634 amu), a second synthetic peptide SEQ ID NO: 2 (YYYYCYYYYY) (hereinafter referred to as a “peptide Y,” mass number: 1588 amu), and a powdery insulin (mass number: 5807 amu) material were dissolved respectively in 2 mL of water containing a small amount of a surfactant (0.1 wt %), the solutions having respectively a concentration of $7.9\times10^{-5}$ mol/L, $1.1\times10^{-5}$ mol/L, and $8.2\times10^{-6}$ mol/L. The solutions are referred to respectively as a “G solution,” a “Y solution,” and an “insulin solution.”

(3) Ten matrixes (having 10 lines and 10 columns), $M_1$ to $M_{10}$ were prepared by use of the G solution and the Y solution in place of the P solution and the Na solution in Example 1 in the same manner for Na matrix formation as in Example 1. The existence quantity units of the G solution, the Y solution, and the insulin solution in one dot are represented respectively by a, b, and c. In every matrix, in the block $B_{ij}$ on the i-th line on the j-th column, the spot at one element position is formed by (i−1) dots of the peptide G (hereinafter G dots), and (j−1) dots of the peptide Y (hereinafter Y dots). Therefore, in that spot, the quantity of the peptide G is a(i−1), and the quantity of the peptide Y is b(j−1). When the number of the element position in the block B is $n_{ij}$, the total quantity of the peptide G in the block $B_{ij}$ is $a(i-1)n_{ij}$, and the total quantity of the peptide Y therein is $b(j-1)n_{ij}$. No dot was put on the block $B_{11}$ on the first line on the first column (at the upper left end) in the respective blocks, so that no spot was formed there.

(4) Onto the spots in the ten matrixes $M_1, \ldots, M_k, \ldots, M_{10}$, including the element positions in the respective blocks $B_{11}$, insulin was dotted in superposition.

On each of the spots in matrix $M_k$, k−1 dots of insulin were put in superposition.

Figure 5A:
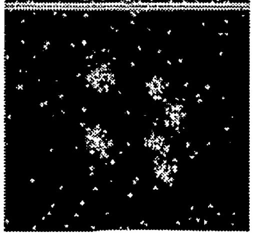
FIGS. 5A, 5B, 5C, 5D, 5E and 5F show measured ion images of secondary ions of specimens on which peptides have been deposited in superposition.
Figure 5B:
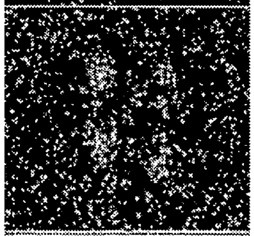
Figure 5C:
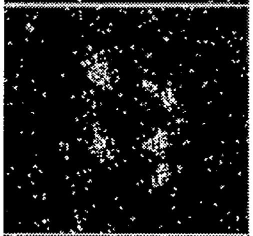
Figure 5D:
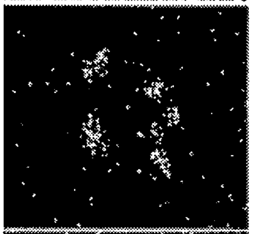
Figure 5E:
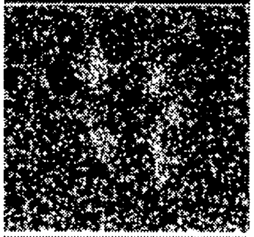
Figure 5F:
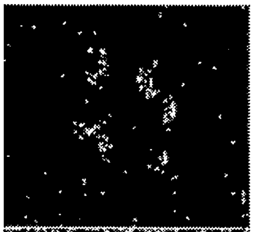

By TOF-SIMS measurement, as shown in FIGS. 5A to 5F, ion images were obtained as secondary ions: ion images of the G peptide parent ions, the Y peptide parent ions and Na atom adducts thereof (FIGS. 5A and 5B), ion images of the Y peptide parent ions, and Na atom adducts thereof (FIGS. 5C and 5D), and ion images of insulin fragments ions (mass number: 804 amu, 1198 amu) (FIGS. 5E and 5F). The quantities of the peptides in the one spot in the ion images were calculated to be 2 pg of the G peptide, 0.7 pg of the Y peptide, and 19 pg of the insulin fragments. In FIGS. 5A to 5F, "mc" and "tc" are abbreviations of "maximum counts" and "total counts," respectively. By combination of the above result with the procedure in Example 2 for "quantitative detection of a chemical reaction product by dropwise addition of aqueous sodium carbonate onto a peptide film substrate," a test of reactivity of several tens of picograms of a peptide with a medical substance (screening) is practicable in principle.

SEQUENCE LISTING FREE TEXT

<210> 1
<223> sample for detection by TOF-SIMS
<210> 2
<223> sample for detection by TOF-SIMS

```
SEQUENCE LISTING

<160> NUMBER OF SEQ ID NOS: 2

<210> SEQ ID NO 1
<211> LENGTH: 10
<212> TYPE: PRT
<213> ORGANISM: Artificial
<220> FEATURE:
<223> OTHER INFORMATION: SAMPLE FOR DETECTION BY TOF-SIMS

<400> SEQUENCE: 1

Gly Gly Gly Gly Cys Gly Gly Gly Gly Gly
1               5                   10


<210> SEQ ID NO 2
<211> LENGTH: 10
<212> TYPE: PRT
<213> ORGANISM: Artificial
<220> FEATURE:
<223> OTHER INFORMATION: SAMPLE FOR DETECTION BY TOF-SIMS

<400> SEQUENCE: 2

Tyr Tyr Tyr Tyr Cys Tyr Tyr Tyr Tyr Tyr
1               5                   10
```

The invention claimed is:

1. A method of analyzing a third chemical substance for a quantity of (i) at least one of a first chemical substance and a second chemical substance and/or (ii) a product of a reaction between the first chemical substance and the second chemical substance, the method comprising:

preparing a calibration curve by:

ejecting droplets of a liquid comprising the first chemical substance for a positive integer number of times to plural independent positions on a first substrate by an inkjet system to apply the first chemical substance for the positive integer number times of an amount contained in one droplet;

ejecting droplets of a liquid comprising the second chemical substance, which can react with the first chemical substance, for a positive integer number of times to positions where the first chemical substance is applied by an inkjet system to apply the second chemical substance for the positive integer number times of an amount contained in one droplet, to thereby prepare a standard sample;

performing a quantitative analysis of the standard sample; and forming the calibration curve based on a result of the quantitative analysis of the standard sample;

performing a quantitative analysis of the third chemical substance provided on another substrate; and Determining, in the third chemical substance, the quantity of (i) at least one of the first chemical substance and the second chemical substance and/or (ii) the product of the reaction between the first chemical substance and the second chemical substance by using a result of the quantitative analysis of the third chemical substance and the calibration curve, wherein, in the preparing of the calibration curve, the droplets are ejected such that the first chemical substance and the second chemical substance are mixed on the applied positions and are at least partially reacted.

2. The method according to claim 1, wherein the quantitative analysis of the standard sample and the quantitative analysis of the third chemical substance are conducted by time-of-flight secondary ion mass spectrometry (TOF-SIMS).

3. The method according to claim 1, wherein the quantitative analysis of the standard sample and the quantitative analysis of the third chemical substance are conducted by one of ionic analysis and fluorescent X-ray analysis.

4. The method according to claim 1, wherein the third chemical substance is analyzed for a quantity of one of the first chemical substance and the second chemical substance.

5. The method according to claim 1, wherein the third chemical substance is analyzed for a quantity of a product of a reaction between the first chemical substance and the second chemical substance.

6. The method of analyzing according to claim 1, wherein the quantitative analysis analysis of the standard sample and the quantitative analysis of the third chemical substance are selected from the group consisting of ionic analysis, fluorescent X-ray analysis, optical response analysis, and electrical conductivity analysis.

* * * * *